United States Patent
Dieckmann et al.

(10) Patent No.: US 9,462,804 B2
(45) Date of Patent: Oct. 11, 2016

(54) AGROCHEMICAL FORMULATIONS COMPRISING CO-POLYMERS BASED ON ETHYLENICALLY UNSATURATED DICARBOXYLIC MONO AND DIESTERS

(75) Inventors: Yvonne Dieckmann, Haßloch (DE); Michael Ishaque, Mannheim (DE); Ingo Münster, Böhl-Iggelheim (DE); Laurent Picard, Bad Bergzabern (DE); Wolfgang Kerl, Mannheim (DE); Jürgen Langewald, Mannheim (DE); Klaus Kreuz, Denzlingen (DE); Harald Köhle, Bobenheim (DE); Felix Christian Görth, Sewickley, PA (US)

(73) Assignee: BASF SE, Ludwigshafen (DE)

( * ) Notice: Subject to any disclaimer, the term of this patent is extended or adjusted under 35 U.S.C. 154(b) by 974 days.

(21) Appl. No.: 12/516,450

(22) PCT Filed: Nov. 9, 2007

(86) PCT No.: PCT/EP2007/062113
§ 371 (c)(1),
(2), (4) Date: May 27, 2009

(87) PCT Pub. No.: WO2008/064986
PCT Pub. Date: Jun. 5, 2008

(65) Prior Publication Data
US 2010/0063167 A1   Mar. 11, 2010

(30) Foreign Application Priority Data
Nov. 30, 2006   (EP) .................................... 06125072

(51) Int. Cl.
*A01N 25/10* (2006.01)
*A01N 25/30* (2006.01)
*A61K 8/90* (2006.01)

(52) U.S. Cl.
CPC ............... *A01N 25/10* (2013.01); *A01N 25/30* (2013.01); *A61K 8/90* (2013.01)

(58) Field of Classification Search
CPC ......... A01N 25/10; A01N 25/30; A61K 8/90
See application file for complete search history.

(56) References Cited

U.S. PATENT DOCUMENTS

| | | | |
|---|---|---|---|
| 5,229,354 A | | 7/1993 | Narayanan et al. |
| 6,071,857 A | * | 6/2000 | Vogt et al. ................... 504/366 |
| 2002/0134012 A1 | | 9/2002 | Ding et al. |
| 2004/0077498 A1 | | 4/2004 | Lynch |
| 2004/0197357 A1 | * | 10/2004 | Heming et al. ............... 424/401 |
| 2005/0090402 A1 | | 4/2005 | Dieing et al. |
| 2006/0047069 A1 | * | 3/2006 | Jakob et al. ................... 525/56 |
| 2010/0048655 A1 | | 2/2010 | Koltzenburg et al. |
| 2010/0120617 A1 | | 5/2010 | Dyllick-Brenzinger et al. |
| 2010/0122379 A1 | | 5/2010 | Dieckmann et al. |

FOREIGN PATENT DOCUMENTS

| | | |
|---|---|---|
| EP | 0 282 951 | 9/1988 |
| EP | 0 551 796 | 7/1993 |
| EP | 875557 A2 * | 11/1998 |
| EP | 1 774 853 | 4/2007 |
| WO | WO 02/21913 | 3/2002 |
| WO | WO 03/043420 | 3/2003 |
| WO | WO 2005/018321 | 3/2005 |
| WO | WO 2006/013972 | 2/2006 |
| WO | WO 2008/040786 | 4/2008 |
| WO | WO 2008/064987 | 6/2008 |
| WO | WO 2008/064990 | 6/2008 |
| WO | WO 2008/065050 | 6/2008 |
| WO | WO 2008/132067 | 11/2008 |
| WO | WO 2008/132179 | 11/2008 |

OTHER PUBLICATIONS

International Search Report completed Jan. 3, 2008, in International Application No. PCT/EP2007/062113, filed Nov. 9, 2007.
International Preliminary Report on Patentability dated Feb. 19, 2009, from corresponding International Application No. PCT/EP2007/062113, filed Nov. 9, 2007.

* cited by examiner

*Primary Examiner* — Kyle Purdy
(74) *Attorney, Agent, or Firm* — Brinks Gilson & Lione

(57) ABSTRACT

The present invention comprises the use of formulations comprising at least one pesticide and at least one co-polymer comprising (a) at least one comonomer (a) selected from the group consisting of olefins, vinylethers, vinyl pyrrolidone and styrene; and (b) at least one comonomer (b) selected from the group consisting of ethylenically unsaturated dicarboxylic mono and diesters, wherein the alcohol moiety of the mono- or diester has the structure of formula I wherein $R^1$ is 1,2-propylene or 2,3 propylene $R^2$ is ethylene; $R^3$ is hydrogen, branched or linear $C_1$-$C_{40}$, preferably $C_1$-$C_{24}$ alkyl, phenyl, phenyl substituted with $C_1$-$C_{20}$ alkyl, benzyl, benzyl substituted with $C_1$-$C_{20}$ alkyl; n corresponds to a value from 0 to 140, preferably 0-50, more preferably 0-20. p corresponds to a value from 0 to 100 wherein the sum of n and p is at least 1, preferably 1-60, most preferably 5-40. in polymerized form, for increasing the systemicity of pesticides, methods for treatment of seeds, methods of improving the health of plants and methods of combating harmful insects and/or phytopathogenic fungi based on the afore-mentioned formulations.

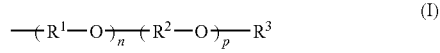

(I)

10 Claims, No Drawings

AGROCHEMICAL FORMULATIONS COMPRISING CO-POLYMERS BASED ON ETHYLENICALLY UNSATURATED DICARBOXYLIC MONO AND DIESTERS

This application is a National Stage application of International Application No. PCT/EP2007/062113 filed Nov. 9, 2007, the entire contents of which is hereby incorporated herein by reference. This application also claims the benefit under 35 U.S.C. §119 of European Patent Application No. 06125072.6, filed Nov. 30, 2006, the entire contents of which is hereby incorporated herein by reference.

The present invention comprises the use of formulations comprising at least one pesticide and at least one co-polymer comprising
(a) at least one comonomer (a) selected from the group consisting of olenfins, vinylethers, vinyl pyrrolidone and styrene; and
(b) at least one comonomer (b) selected from the group consisting of ethylenically unsaturated dicarboxylic mono and diesters, wherein the alcohol mojety of the mono- or diester has the structure of formula I

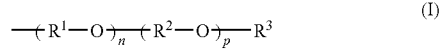

wherein
$R^1$ is 1,2-propylene or 2,3 propylene
$R^2$ is ethylene;
$R^3$ is hydrogen, branched or linear $C_1$-$C_{40}$, preferably $C_1$-$C_{24}$ alkyl, phenyl, phenyl substituted with $C_1$-$C_{20}$ alkyl, benzyl, benzyl substituted with $C_1$-$C_{20}$ alkyl;
n corresponds to a value from 0 to 140, preferably 0-50, more preferably 0-20.
p corresponds to a value from 0 to 100 wherein the sum of n and p is at least 1, preferably 1-60, most preferably 5-40.

in polymerized form, for increasing the systemicity of pesticides, methods for treatment of seeds, methods of improving the health of plants and methods of combating harmful insects and/or phytopathogenic fungi based on the afore-mentioned formulations.

Systemic pesticides provide the farmer lots of benefits: The uptake of pesticide of plants, which can be achieved either by seed treatment, foliar treatment or soil treatment, which is the simultaneous or sequential application of seeds and respective formulation (e.g. granule formulations), leads to plants, which are much longer resistant towards pests than plants treated with non-systemic pesticides.

Also for pesticides which provide plant health effects it is desirable to increase their uptake in the plant. The term "plant health" describes for example, advantageous properties such as improved crop characteristics including, but not limited to better emergence, increased crop yields, more favourable protein and/or content, more favourable amino-acid and/or oil composition, more developed root system (improved root growth), tillering increase, increase in plant height, bigger leaf blade, less dead basal leaves, stronger tillers, greener leaf colour, pigment content, photosynthetic activity, less fertilizers needed, less seeds needed, more productive tillers, earlier flowering, early grain maturity, less plant verse (lodging), increased shoot growth, enhanced plant vigor, increased plant stand or early germination; or a combination of at least two or more of the aforementioned effects or any other advantages familiar to a person skilled in the art.

Many pesticides, however, do not show satisfactory systemicity. Furthermore, the systemicity of already systemic pesticides leaves room for improvement.

It is therefore an object of the present invention to improve the systemicity of pesticides, preferably of pesticides with low or no systemicity.

Numerous polymers that can be used for agrochemical formulation (e.g. for controlled release, or which are simply be useful) as solubilizers) are known in the art.

EP 282951-A for example describes co-polymers based on maleic anhydride and polyalkylene glycol ether, for the preparation of controlled release formulations.

U.S. Pat. No. 5,229,354 describes leaching inhibition of pesticides with nitrogen containing polymers, which are based on acrylic acid derivatives and derivatives of ethylencially unsaturated mono or di-carboxylic acids, wherein said mono- or diester derivatives comprise an optionally quaternized amino-group.

US 2002/0134012 describes seed coating compositions providing controlled release of pesticides, wherein in a first step, the respective seed is treated with a pesticide and in a second step coated with a non-pesticide comprising coating layer. For that coating layer, numerous polymers are suitable, inter alia maleic acid/styrene copolymer.

US 2004/0074498 also describes seed coating compositions, wherein in a first step, the respective seed is coated with a non-pesticide comprising coating layer for preventing phytotoxic effects and in a second step treated with a pesticide. For that coating layer, numerous polymers are suitable, inter alia maleic acid/styrene copolymer.

WO 02/21913 describes controlled release formulations for pesticides, wherein the pesticide is entrapped in a matrix polymer. Numerous polymers are suitable matrix polymers, inter alia poly(styrene-co maleic acid anhydride).

WO 03/043420 describes copolmyers comprising an olefin and/or an vinyl ether and ethylenically unsaturated dicarboxylic acid and/or at least one ethylenically unsaturated dicarboxylic acid derivatives as adjuvants.

WO 05/018321 describe amphiphilic copolymers comprising ethylenically unsaturated dicarboxylic acid or an ethylenically unsaturated dicarboxylic acid derivatives as adjuvants.

However, whether any of these polymers is suitable for increasing the systemicity of pesticides is not disclosed in prior art.

The object of the present invention was achieved by the use of at least one copolymer, which increases the systemicity of pesticides, preferably of pesticides with low or no systemicity, wherein the copoylmer comprises
(a) at least one comonomer (a) selected from the group consisting of olenfins, vinylethers, vinyl pyrrolidone and styrene; and
(b) at least one comonomer (b) selected from the group consisting of ethylenically unsaturated dicarboxylic mono and diesters, wherein the alcohol moiety of the mono- or diester has the structure described in formula I

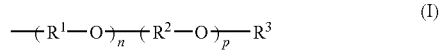

wherein
$R^1$ is 1,2-propylene or 2,3 propylene
$R^2$ is ethylene;

$R^3$ is hydrogen, branched or linear $C_1$-$C_{40}$, preferably $C_1$-$C_{24}$ alkyl, phenyl, phenyl substituted with $C_1$-$C_{20}$ alkyl, benzyl, benzyl substituted with $C_1$-$C_{20}$ alkyl;

n corresponds to a value from 0 to 140, preferably 0-50, more preferably 0-20.

p corresponds to a value from 0 to 100 wherein the sum of n and p is at least 1, preferably 1-60, most preferably 5-40.

in polymerized form.

The term at least one means that one or more co-polymers as defined above can be present in the above-mentioned formulation, i.e. also mixtures of the above-defined copolymers. Preferably, 1, 2 or 3, more preferably 1 or 2 most preferably 1 copolymer present in the above-mentioned formulation.

In a particular preferred embodiment, n is 0; and p is 10-30, preferably 15-25, most preferably 18-22, wherein 20 is particularly preferred.

In another particular preferred embodiment n is 1-10; and p is 10-20,

Ethylenically unsaturated dicarboxylic mono and diesters are preferably derived from unsaturated dicarboxylic acids with 4 to 8 and in particular 4 to 6 carbon atoms, for example maleic acid, itaconic acid, mesaconic acid, citraconic acid and methylene-malonic acid. Especially preferred among these carboxylic acids are itaconic acid and, for practical reasons, maleic acid. Preferred are the afore-defined monoesters.

The term "$C_1$-$C_{20}$-alkyl" as used herein refers to a branched or unbranched saturated hydrocarbon group having 1 to 20 carbon atoms, for example methyl, ethyl, propyl, i-propyl, butyl, tert.-butyl, 2-methyl-propyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methyl pentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl, iso-nonyl, n-decyl, iso-decyl, n-undecyl, iso-undecyl, n-dodecyl, iso-dodecyl, n-tridecyl, iso-tridecyl, stearyl and n-eicosyl and their isomers and decyl and their isomers.

The term "$C_1$-$C_{40}$-alkyl" as used herein refers to a branched or unbranched saturated hydrocarbon group having 1 to 40 carbon atoms including those examples listed for $C_1$-$C_{20}$ alkyl.

The above-mentioned co-polymers of formula I may be statistic co-polymers or block co-polymers.

If the above-mentioned co-polymers of formula I are block-copolymers, the respective blocks may be arranged as set forth in formula Ia

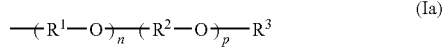

$$-(R^1-O)_n-(R^2-O)_p-R^3 \quad \text{(Ia)}$$

or formula Ib

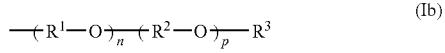

$$-(R^1-O)_n-(R^2-O)_p-R^3 \quad \text{(Ib)}$$

wherein the substituents have the meaning as given above.

In one preferred embodiment, $R^3$ is a phenyl radical which may be substituted or un-substituted with 1, 2, 3 or 4 identical or different substituents L, wherein L is $C_1$-$C_{20}$ alkyl, wherein saturated straight-chain or branched hydrocarbon radicals having from 1 to 20 carbon atoms, preferably $C_1$-$C_{12}$ are preferred, and straight-chain $C_1$-$C_{12}$ such as methyl, ethyl, propyl, butyl, pentyl, hexyl, heptyl, octoyl, nonyl, decyl undecyl, duodecyl, most preferably nonyl are most preferred.

In a particular preferred embodiment, $R^3$ is a phenyl radical, substituted with one nonlymojety, preferably 4-nonlyphenyl radical.

Suitable olefins include $C_4$ to $C_{40}$ olefins, preferably α-olefins, which may be straight chain or branched such as, for example, but-1-ene, but-2-ene, butadiene, 2-methylprop-1-ene (isobutene), pent-1-ene, isoprene, 2-methylbut-1-ene, 3-methylbut-1-ene, hex-1-ene, cyclohexadiene, 2-methylpent-1-ene, 3-methylpent-1-ene, 4-methylpent-1-ene, 2-ethylbut-1-ene, 4,4-dimethylbut-1-ene, 2,4-dimethylbut-1-ene, 2,3-dimethylpent-1-ene, 3,3-dimethylpent-1-ene, 2,4-dimethylpent-1-ene, 3,4-dimethylpent-1-ene, 4,4-dimethylpent-1-ene, oct-1-ene, 2,4,4-trimethylpent-1-ene, 2,4,4-trimethylpent-2-ene, diisobutylene, in particular one which presents itself technically as an isomer mixture of, essentially, 2,4,4-trimethylpent-1-ene and 2,4,4-trimethylpent-2-ene, for example in a ratio of approx. 80% by weight to approx. 20% by weight, 4,4-dimethylhex-1-ene, 2-ethylhex-1-ene, oligo- and polyisobutenes with a molecular weight of less than 2.000, oligopropenes with a molecular weight of less than 1.000, dec-1-ene, dodec-1-ene, tetradec-1-ene, hexadec-1-ene, heptadec-1-ene, octadec-1-ene, $C_{18}$-olefin-1, $C_{20}$-olefin-1, $C_{22}$-olefin-1, $C_{24}$-olefin-1, $C_{20}$ to $C_{24}$-olefin-1, $C_{24}$- to $C_{28}$-olefin-1, $C_{30}$-olefin-1, $C_{35}$-olefin-1, $C_{35}$-olefin-1, styrene, alkyl-substituted styrenes such as alpha-methylstyrene, tert-butylstyrene, vinyltoluene, cyclic olefins such as cyclooctene, and mixtures of these comonomers.

In one embodiment, straight chain α-olefins are preferred, more preferred $C_{12}$-$C_{28}$ straight chain α-olefins. Most preferably $C_{12}$ and $C_{20}$ olefins or mixtures of $C_{20}$-$C_{24}$ olefins are used.

In another embodiment, branched α-olefins are preferred, wherein $C_8$ branched α-olefins such as 2,4,4-trimethylpentene or diisobutylene are most preferred Vinyl ethers which are suitable for the comonomer units (i) are vinyl ethers whose alcohol moiety has 1 to 30 and preferably 1 to 20 carbon atoms. $C_1$-$C_{30}$-Alkyl vinyl ethers must be mentioned in particular in this context, it being possible for the alkyl radicals to be linear, branched or cyclic, unsubstituted or substituted. Examples of suitable alkyl vinyl ethers are methyl vinyl ether, ethyl vinyl ether, propyl vinyl ether, isopropyl vinyl ether, butyl vinyl ether, dodecyl vinyl ether, butyl dodecyl vinylether, preferably methyl-octadecyl vinylether, butyl-dodecyl vinylether, dodecylvinylether The copolymers can be synthesized according to methods known in the art, for example by those referred to in WO 03/043420.

All embodiments of the above-mentioned polymers are referred herein below as "polymers according to the present invention".

The use of polymers according to the present invention for increasing the systemicity of pesticides is achieved contacting the pesticide with a certain amount of polymer according to the present invention e.g. in an agrochemical formulation comprising at least one pesticide and at least one polymer according to the present invention.

Herein, the polymer according to the present invention can be added to an already prepared formulation or included in a formulation comprising at least one pesticide and at least one polymer according to the present invention. The addition of the polymer to the formulation can be performed prior or after dilution of the formulation in water; e.g. preparing a formulation as mentioned before containing the polymer according to this invention or adding the polymer after dilution of the pesticide formulation in water e.g. so called tank mix).

The weight by weight ratio of polymer:pesticide is preferably 20:1-1:20, more preferably 10:1-1:10, most preferably 3:1-1:3.

In general, the formulations comprise from 0.1 to 99% by weight of the polymer according to the present invention, preferably from 1 to 85% by weight, more preferably from 3 to 70% by weight, most preferably from 5 to 60% by weight.

In general, the formulations comprise from 0.1 to 90% by weight, preferably from 1 to 85% by weight, of the pesticide(s), more preferably from 3 to 80% by weight, most preferably from 3 to 70% by weight.

The term "at least one pesticide" within the meaning of the invention states that one or more compounds can be selected from the group consisting of fungicides, insecticides, nematicides, herbicide and/or safener or growth regulator, preferably from the group consisting of fungicides, insecticides or nematicides, most preferably from the group consisting of fungicides. Also mixtures of pesticides of two or more the aforementioned classes can be used. The skilled artisan is familiar with such pesticides, which can be, for example, found in the Pesticide Manual, 13th Ed. (2003), The British Crop Protection Council, London.

The following list of pesticides is intended to illustrate the possible combinations, but not to impose any limitation: The insecticide/nematicide is selected from the group consisting of The following list of pesticides together with which the compounds according to the invention can be used, is intended to illustrate the possible combinations, but not to impose any limitation:

A.1. Organo(thio)phosphates: acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos, trichlorfon;
A.2. Carbamates: alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicarb, triazamate;
A.3. Pyrethroids: allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin, profluthrin, dimefluthrin;
A.4. Growth regulators: a) chitin synthesis inhibitors: benzoylureas: chlorfluazuron, diflubenzuron, flucycloxuron, flufenoxuron, hexaflumuron, lufenuron, novaluron, teflubenzuron, triflumuron; buprofezin, diofenolan, hexythiazox, etoxazole, clofentazine; b) ecdysone antagonists: halofenozide, methoxyfenozide, tebufenozide, azadirachtin; c) juvenoids: pyriproxyfen, methoprene, fenoxycarb; d) lipid biosynthesis inhibitors: spirodiclofen, spiromesifen, spirotetramat;
A.5. Nicotinic receptor agonists/antagonists compounds: clothianidin, dinotefuran, imidacloprid, thiamethoxam, nitenpyram, acetamiprid, thiacloprid; the thiazol compound of formula ($\Delta^1$)

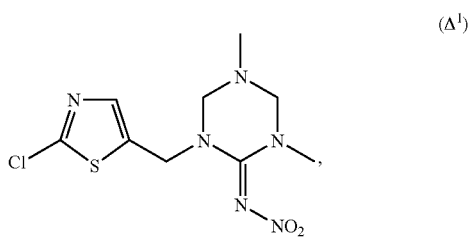 [SMILES: CN1CN(C)/C(=N\[N+](=O)[O-])N(Cc2cnc(Cl)s2)C1]

($\Delta^1$)

A.6. GABA antagonist compounds: acetoprole, endosulfan, ethiprole, fipronil, vaniliprole, pyrafluprole, pyriprole, the phenylpyrazole compound of formula $\Delta^2$

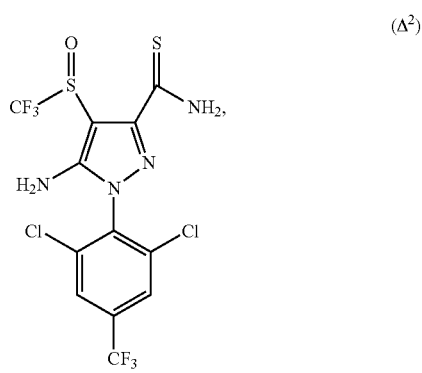 [SMILES: NC(=S)c1nn(-c2c(Cl)cc(C(F)(F)F)cc2Cl)c(N)c1S(=O)C(F)(F)F]

($\Delta^2$)

A.7. Macrocyclic lactone insecticides: abamectin, emamectin, milbemectin, lepimectin, spinosad, the compound of formula ($\Delta^3$) (CAS No. 187166-40-1)

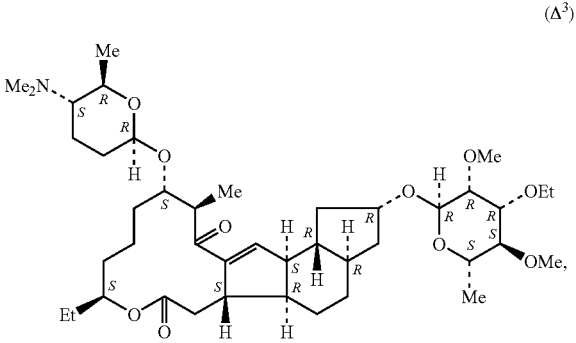

($\Delta^3$)

A.8. METI I compounds: fenazaquin, pyridaben, tebufenpyrad, tolfenpyrad, flufenerim;
A.9. METI II and III compounds: acequinocyl, fluacyprim, hydramethylnon;
A.10. Uncoupler compounds: chlorfenapyr;
A.11. Oxidative phosphorylation inhibitor compounds: cyhexatin, diafenthiuron, fenbutatin oxide, propargite;

A.12. Moulting disruptor compounds: cyromazine;
A.13. Mixed Function Oxidase inhibitor compounds: piperonyl butoxide;
A.14. Sodium channel blocker compounds: indoxacarb, metaflumizone,
A.15. Various: benclothiaz, bifenazate, cartap, flonicamid, pyridalyl, pymetrozine, sulfur, thiocyclam, flubendiamide, cyenopyrafen, flupyrazofos, cyflumetofen, amidoflumet, the aminoquinazolinone compound of formula $\Delta^4$

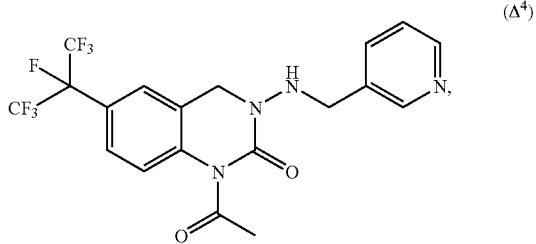

N—R'-2,2-dihalo-1-R"cyclo-propanecarboxamide-2-(2,6-dichloro-α,α,α-tri-fluoro-p-tolyl)hydrazone or N—R'-2,2-di(R''')propionamide-2-(2,6-dichloro-α,α,α-trifluoro-p-tolyl)-hydrazone, wherein R' is methyl or ethyl, halo is chloro or bromo, R" is hydrogen or methyl and R''' is methyl or ethyl, anthranilamide compounds of formula $\Delta^5$

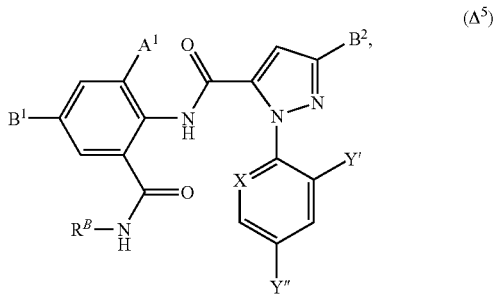

wherein $A^1$ is $CH_3$, Cl, Br, I, X is C—H, C—Cl, C—F or N, Y' is F, Cl, or Br, Y" is F, Cl, $CF_3$, $B^1$ is hydrogen, Cl, Br, I, CN, $B^2$ is Cl, Br, $CF_3$, $OCH_2CF_3$, $OCF_2H$, and $R^B$ is hydrogen, $CH_3$ or $CH(CH_3)_2$, and malononitrile compounds as described in JP 2002 284608, WO 02/89579, WO 02/90320, WO 02/90321, WO 04/06677, WO 04/20399, or JP 2004 99597.

The commercially available compounds of the group A may be found in The Pesticide Manual, 13$^{th}$ Edition, British Crop Protection Council (2003) among other publications. Thiamides of formula $\Delta^2$ and their preparation have been described in WO 98/28279. Lepimection is known from Agro Project, PJB Publications Ltd, November 2004. Benclothiaz and its preparation have been described in EP-A1 454621. Methidathion and Paraoxon and their preparation have been described in Farm Chemicals Handbook, Volume 88, Meister Publishing Company, 2001. Acetoprole and its preparation have been described in WO 98/28277. Metaflumizone and its preparation have been described in EP-A1 462 456. Flupyrazofos has been described in Pesticide Science 54, 1988, p. 237-243 and in U.S. Pat. No. 4,822,779. Pyrafluprole and its preparation have been described in JP 2002193709 and in WO 01/00614. Pyriprole and its preparation have been described in WO 98/45274 and in U.S. Pat. No. 6,335,357. Amidoflumet and its preparation have been described in U.S. Pat. No. 6,221,890 and in JP 21010907. Flufenerim and its preparation have been described in WO 03/007717 and in WO 03/007718. Cyflumetofen and its preparation have been described in WO 04/080180.

Anthranilamides of formula $\Delta^5$ and their preparation have been described in WO 01/70671; WO 02/48137; WO 03/24222, WO 03/15518, WO 04/67528; WO 04/33468; and WO 05/118552.

The fungicide can be selected from the group consisting of
1. Strobilurins such as azoxystrobin, dimoxystrobin, enestroburin, fluoxastrobin, kresoxim-methyl, metominostrobin, picoxystrobin, pyraclostrobin, trifloxystrobin, orysastrobin, methyl (2-chloro-5-[1-(3-methylbenzyloxyimino)ethyl]benzyl)carbamate, methyl (2-chloro-5-[1-(6-methylpyridin-2-ylmethoxyimino)ethyl]benzyl)carbamate, methyl 2-(ortho-((2,5-dimethylphenyloxymethylene)phenyl)-3-methoxyacrylate;
2. Carboxamides such as
carboxanilides: benalaxyl, benodanil, boscalid, carboxin, mepronil, fenfuram, fenhexamid, flutolanil, furametpyr, metalaxyl, ofurace, oxadixyl, oxycarboxin, penthiopyrad, thifluzamide, tiadinil, N-(4'-bromobiphenyl-2-yl)-4-difluoromethyl-2-methylthiazole-5-carboxamide, N-(4'-trifluoromethylbiphenyl-2-yl)-4-difluoromethyl-2-methylthiazole-5-carboxamide, N-(4'-chloro-3'-fluorobiphenyl-2-yl)-4-difluoromethyl-2-methylthiazole-5-carboxamide, N-(3',4'-dichloro-4-fluorobiphenyl-2-yl)-3-difluoromethyl-1-methylpyrazole-4-carboxamide, N-(2-cyanophenyl)-3,4-dichloroisothiazole-5-carboxamide;
carboxylic acid morpholides: dimethomorph, flumorph;
benzamides: flumetover, fluopicolide (picobenzamid), zoxamide;
other carboxamides: carpropamid, diclocymet, mandipropamid, N-(2-(4-[3-(4-chlorophenyl)prop-2-ynyloxy]-3-methoxyphenypethyl)-2-methanesulfonylamino-3-methylbutyramide, N-(2-(4-[3-(4-chlorophenyl)prop-2-ynyloxy]-3-methoxyphenypethyl)-2-ethanesulfonylamino-3-methylbutyramide, N-(3',4'-dichloro-5-fluorobiphenyl-2-yl)-3-difluoromethyl-1-methylpyrazole-4-carboxamide and 3-Difluoromethyl-1-methyl-1H-pyrazole-4-carboxylic acid (2-bicyclopropyl-2-yl-phenyl)-amide;
3. Azoles such as
triazoles: bitertanol, bromuconazole, cyproconazole, difenoconazole, diniconazole, enilconazole, epoxiconazole, fenbuconazole, flusilazole, fluquinconazole, flutriafol, hexaconazole, imibenconazole, ipconazole, metconazole, myclobutanil, penconazole, propiconazole, prothioconazole, simeconazole, tebuconazole, tetraconazole, triadimenol, triadimefon, triticonazole;
imidazoles: cyazofamid, imazalil, pefurazoate, prochloraz, triflumizole; benzimidazoles: benomyl, carbendazim, fuberidazole, thiabendazole; others: ethaboxam, etridiazole, hymexazole;
4. Nitrogenous heterocyclyl compounds such as
pyridines: fluazinam, pyrifenox, 3-[5-(4-chlorophenyl)-2,3-dimethylisoxazolidin-3-yl]-pyridine;
pyrimidines: bupirimate, cyprodinil, ferimzone, fenarimol, mepanipyrim, nuarimol, pyrimethanil;
piperazines: triforine;
pyrroles: fludioxonil, fenpiclonil;
morpholines: aldimorph, dodemorph, fenpropimorph, tridemorph;
dicarboximides: iprodione, procymidone, vinclozolin;
others: acibenzolar-5-methyl, anilazine, captan, captafol, dazomet, diclomezine, fenoxanil, folpet, fenpropidin, famoxadone, fenamidone, octhilinone, probenazole, proquinazid, pyroquilon, quinoxyfen, tricyclazole, 5-chloro-7-(4-methylpiperidin-1-yl)-6-(2,4,6-trifluorophenyl)-[1,2,4]triazolo[1,5-a]pyrimidine, 2-butoxy-6-iodo-3-propylchromen-4-one, N,N-dimethyl-3-(3-bromo-6-fluoro-2-methylindole-1-sulfonyl)-[1,2,4]triazole-1-sulfonamide;

5. Carbamates and dithiocarbamates such as
dithiocarbamates: ferbam, mancozeb, maneb, metiram, metam, propineb, thiram, zineb, ziram;
carbamates: diethofencarb, flubenthiavalicarb, iprovalicarb, propamocarb, methyl 3-(4-chlorophenyl)-3-(2-isopropoxycarbonylamino-3-methylbutyrylamino)propionate, 4-fluorophenyl N-(1-(1-(4-cyanophenyl)ethanesulfonyl)but-2-yl)carbamate;

6. Other fungicides such as
guanidines: dodine, iminoctadine, guazatine;
antibiotics: kasugamycin, polyoxins, streptomycin, validamycin A;
organometallic compounds: fentin salts;
sulfur-containing heterocyclyl compounds: isoprothiolane, dithianon;
organophosphorus compounds: edifenphos, fosetyl, fosetyl-aluminum, iprobenfos, pyrazophos, tolclofos-methyl, phosphorous acid and its salts;
organochlorine compounds: thiophanate-methyl, chlorothalonil, dichlofluanid, tolylfluanid, flusulfamide, phthalide, hexachlorbenzene, pencycuron, quintozene;
nitrophenyl derivatives: binapacryl, dinocap, dinobuton;
inorganic active compounds: Bordeaux mixture, copper acetate, copper hydroxide, copper oxychloride, basic copper sulfate, sulfur;
others: spiroxamine, cyflufenamid, cymoxanil, metrafenone.

The herbicide is selected from the group consisting of
b1) lipid biosynthesis inhibitors such as chlorazifop, clodinafop, clofop, cyhalofop, diclofop, fenoxaprop, fenoxaprop-p, fenthiaprop, fluazifop, fluazifop-P, haloxyfop, haloxyfopP, isoxapyrifop, metamifop, propaquizafop, quizalofop, quizalofop-P, trifop, alloxydim, butroxydim, clethodim, cloproxydim, cycloxydim, profoxydim, sethoxydim, tepraloxydim, tralkoxydim, butylate, cycloate, diallate, dimepiperate, EPTC, esprocarb, ethiolate, isopolinate, methiobencarb, molinate, orbencarb, pebulate, prosulfocarb, sulfallate, thiobencarb, tiocarbazil, triallate, vernolate, benfuresate, ethofumesate and bensulide;
b2) ALS inhibitors such as amidosulfuron, azimsulfuron, bensulfuron, chlorimuron, chlorsulfuron, cinosulfuron, cyclosulfamuron, ethametsulfuron, ethoxysulfuron, flazasulfuron, flupyrsulfuron, foramsulfuron, halosulfuron, imazosulfuron, iodosulfuron, mesosulfuron, metsulfuron, nicosulfuron, oxasulfuron, primisulfuron, prosulfuron, pyrazosulfuron, rimsulfuron, sulfometuron, sulfosulfuron, thifensulfuron, triasulfuron, tribenuron, trifloxysulfuron, triflusulfuron, tritosulfuron, imazamethabenz, imazamox, imazapic, imazapyr, imazaquin, imazethapyr, cloransulam, diclosulam, florasulam, flumetsulam, metosulam, penoxsulam, bispyribac, pyriminobac, propoxycarbazone, flucarbazone, pyribenzoxim, pyriftalid and pyrithiobac;
b3) photosynthesis inhibitors such as atraton, atrazine, ametryne, aziprotryne, cyanazine, cyanatryn, chlorazine, cyprazine, desmetryne, dimethametryne, dipropetryn, eglinazine, ipazine, mesoprazine, methometon, methoprotryne, procyazine, proglinazine, prometon, prometryne, propazine, sebuthylazine, secbumeton, simazine, simeton, simetryne, terbumeton, terbuthylazine, terbutryne, trietazine, ametridione, amibuzin, hexazinone, isomethiozin, metamitron, metribuzin, bromacil, isocil, lenacil, terbacil, brompyrazon, chloridazon, dimidazon, desmedipham, phenisopham, phenmedipham, phenmedipham-ethyl, benzthiazuron, buthiuron, ethidimuron, isouron, methabenzthiazuron, monoisouron, tebuthiuron, thiazafluoron, anisuron, buturon, chlorbromuron, chloreturon, chlorotoluron, chloroxuron, difenoxuron, dimefuron, diuron, fenuron, fluometuron, fluothiuron, isoproturon, linuron, methiuron, metobenzuron, metobromuron, metoxuron, monolinuron, monuron, neburon, parafluoron, phenobenzuron, siduron, tetrafluoron, thidiazuron, cyperquat, diethamquat, difenzoquat, diquat, morfamquat, paraquat, bromobonil, bromoxynil, chloroxynil, iodobonil, ioxynil, amicarbazone, bromofenoxim, flumezin, methazole, bentazone, propanil, pentanochlor, pyridate, and pyridafol;
b4) protoporphyrinogen-IX oxidase inhibitors such as acifluorfen, bifenox, chlomethoxyfen, chlornitrofen, ethoxyfen, fluorodifen, fluoroglycofen, fluoronitrofen, fomesafen, furyloxyfen, halosafen, lactofen, nitrofen, nitrofluorfen, oxyfluorfen, fluazolate, pyraflufen, cinidon-ethyl, flumiclorac, flumioxazin, flumipropyn, fluthiacet, thidiazimin, oxadiazon, oxadiargyl, azafenidin, carfentrazone, sulfentrazone, pentoxazone, benzfendizone, butafenacil, pyraclonil, profluazol, flufenpyr, flupropacil, nipyraclofen and etnipromid;
b5) bleacher herbicides such as metflurazon, norflurazon, flufenican, diflufenican, picolinafen, beflubutamid, fluridone, fluorochloridone, flurtamone, mesotrione, sulcotrione, isoxachlortole, isoxaflutole, benzofenap, pyrazolynate, pyrazoxyfen, benzobicyclon, amitrole, clomazone, aclonifen, 4-(3-trifluoromethylphenoxy)-2-(4-trifluoromethylphenyl)pyrimidine, and also 3-heterocyclyl-substituted benzoyl derivatives of the formula II (see in WO 96/26202, WO 97/41116, WO 97/41117 and WO 97/41118)

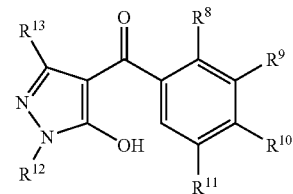

in which the variables $R^8$ to $R^{13}$ are as defined below:
$R^8$, $R^{10}$ are hydrogen, halogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-alkylsulfinyl or $C_1$-$C_6$-alkylsulfonyl;
$R^9$ is a heterocyclic radical selected from the group consisting of such as thiazol-2-yl, thiazol-4-yl, thiazol-5-yl, isoxazol-3-yl, isoxazol-4-yl, isoxazol-5-yl, 4,5-dihydroisoxazol-3-yl, 4,5-dihydroisoxazol-4-yl and 4,5-dihydroisoxazol-5-yl, where the nine radicals mentioned may be unsubstituted or mono- or polysubstituted, e.g. mono-, di-, tri- or tetrasubstituted, by halogen, $C_1$-$C_4$-alkyl, $C_1$-$C_4$-alkoxy, $C_1$-$C_4$-haloalkyl, $C_1$-$C_4$-haloalkoxy or $C_1$-$C_4$-alkylthio;
$R^{11}$ is hydrogen, halogen or $C_1$-$C_6$-alkyl;
$R^{12}$ is $C_1$-$C_6$-alkyl;
$R^{13}$ is hydrogen or $C_1$-$C_6$-alkyl.
b6) EPSP synthase inhibitors such as glyphosate;
b7) glutamine synthase inhibitors such as glufosinate and bilanaphos;
b8) DHP synthase inhibitors such as asulam;
b9) mitose inhibitors such as benfluralin, butralin, dinitramine, ethalfluralin, fluchloralin, isopropalin, methalpropalin, nitralin, oryzalin, pendimethalin, prodiamine, profluralin, trifluralin, amiprofos-methyl, butamifos, dithiopyr, thiazopyr, propyzamide, tebutam, chlorthal, carbetamide, chlorbufam, chlorpropham and propham;

b10) VLCFA inhibitors such as acetochlor, alachlor, butachlor, butenachlor, delachlor, diethatyl, dimethachlor, dimethenamid, dimethenamid-P, metazachlor, metolachlor, S-metolachlor, pretilachlor, propachlor, propisochlor, prynachlor, terbuchlor, thenylchlor, xylachlor, allidochlor, CDEA, epronaz, diphenamid, napropamide, naproanilide, pethoxamid, flufenacet, mefenacet, fentrazamide, anilofos, piperophos, cafenstrole, indanofan and tridiphane;

b11) cellulose biosynthesis inhibitors such as dichlobenil, chlorthiamid, isoxaben and flupoxam;

b12) decoupler herbicides such as dinofenate, dinoprop, dinosam, dinoseb, dinoterb, DNOC, etinofen and medinoterb;

b13) auxin herbicides such as clomeprop, 2,4-D, 2,4,5-T, MCPA, MCPA thioethyl, dichlorprop, dichlorprop-P, mecoprop, mecoprop-P, 2,4-DB, MCPB, chloramben, dicamba, 2,3,6-TBA, tricamba, quinclorac, quinmerac, clopyralid, fluoroxypyr, picloram, triclopyr and benazolin;

b14) auxin transport inhibitors such as naptalam, diflufenzopyr;

b15) benzoylprop, flamprop, flamprop-M, bromobutide, chlorflurenol, cinmethylin, methyldymron, etobenzanid, fosamine, metam, pyributicarb, oxaziclomefone, dazomet, triaziflam and methyl bromide.

Suitable safeners can be selected from the following listing: benoxacor, cloquintocet, cyometrinil, dichlormid, dicyclonon, dietholate, fenchlorazole, fenclorim, flurazole, fluxofenim, furilazole, isoxadifen, mefenpyr, mephenate, naphthalic anhydride, 2,2,5-trimethyl-3-(dichloroacetyl)-1, 3-oxazolidine (R-29148), 4-(dichloroacetyl)-1-oxa-4-azaspiro[4.5]decane (AD-67; MON 4660) and oxabetrinil Generally, fungicides and insecticides are preferred.

Preferred insecticides are azinphos-methyl, chlorpyrifos, chlorpyrifos-methyl, chlorfenvinphos, diazinon, disulfoton, ethion, fenitrothion, fenthion, isoxathion, malathion, methidathion, methyl-parathion, parathion, phenthoate, phosalone, phosmet, phorate, phoxim, pirimiphos-methyl, profenofos, prothiofos, sulprophos, tetrachlorvinphos, terbufos, alanycarb, benfuracarb, carbosulfan, fenoxycarb, furathiocarb, methiocarb, triazamate; chlorfluazuron, diflubenzuron, flucycloxuron, flufenoxuron, hexaflumuron, lufenuron, novaluron, teflubenzuron, triflumuron; methoxyfenozide, tebufenozide, azadirachtin pyriproxyfen, methoprene, fenoxycarb; spirodiclofen, spiromesifen, spirotetramat; clothianidin, dinotefuran, imidacloprid, thiamethoxam, nitenpyram, acetamiprid, thiacloprid; acetoprole, endosulfan, ethiprole, fipronil, vaniliprole, pyrafluprole, pyriprole, the phenylpyrazole compound of formula $\Delta^2$

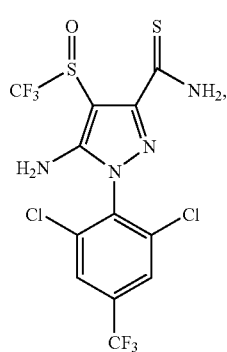

($\Delta^2$)

abamectin, emamectin, milbemectin, lepimectin, fenazaquin, pyridaben, tebufenpyrad acequinocyl, fluacyprim, hydramethylnon, chlorfenapyr, cyhexatin, diafenthiuron, fenbutatin oxide, propargite, piperonyl butoxide; indoxacarb, metaflumizone, bifenazate, pymetrozine, N—R'-2,2-dihalo-1-R"cyclo-propanecarboxamide-2-(2,6-dichloro-α, α,α-tri-fluoro-p-tolyl)hydrazone or N—R'-2,2-di(R''') propionamide-2-(2,6-dichloro-α,α,α-trifluoro-p-tolyl)-hydrazone, wherein R' is methyl or ethyl, halo is chloro or bromo, R" is hydrogen or methyl and R''' is methyl or ethyl More preferred insecticides are cyfluthrin, λ-cyhalothrin, cypermethrin, alpha-cypermethrin, beta-cypermethrin, deltamethrin, esfenvalerate, fenvalerate, permethrin, tefluthrin, tetramethrin, transfluthrin, flufenoxuron, teflubenzuron, clothianidin, thiamethoxam, acetamiprid, ethiprole, fipronil, phenylpyrazole compound of formula $\Delta^2$

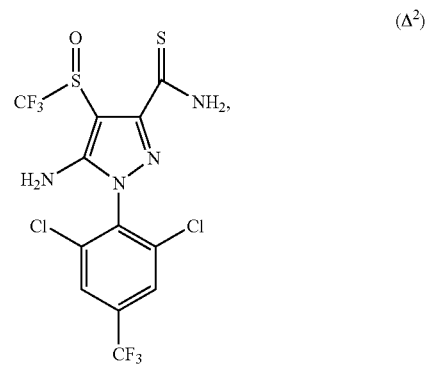

($\Delta^2$)

chlorfenapyr; piperonyl butoxide:indoxacarb, metaflumizone, pymetrozine, N—R'-2,2-dihalo-1-R"cyclo-propanecarboxamide-2-(2,6-dichloro-α,α,α-tri-fluoro-p-tolyl)hydrazone or N—R'-2,2-di(R''')propionamide-2-(2,6-dichloro-α,α,α-trifluoro-p-tolyl)-hydrazone, wherein R' is methyl or ethyl, halo is chloro or bromo, R" is hydrogen or methyl and R''' is methyl or ethyl.

Preferred fungicides are are azoxystrobin, dimoxystrobin, fluoxastrobin, kresoxim-methyl, picoxystrobin, pyraclostrobin, trifloxystrobin, orysastrobin, methyl 2-(ortho-((2,5-dimethylphenyloxymethylene)phenyl)-3-methoxyacrylate; boscalid, metalaxyl, penthiopyrad, N-(3',4'-dichloro-4-fluorobiphenyl-2-yl)-3-difluoromethyl-1-methylpyrazole-4-carboxamide, dimethomorph, fluopicolide (picobenzamid), zoxamide; mandipropamid, N-(3',4'-dichloro-5-fluorobiphenyl-2-yl)-3-difluoromethyl-1-methylpyrazole-4-carboxamide, 3-Difluoromethyl-1-methyl-1H-pyrazole-4-carboxylic acid (2-bicyclopropyl-2-yl-phenyl)-amide, cyproconazole, difenoconazole, epoxiconazole, fluquinconazole, metconazole, propiconazole, prothioconazole, tebuconazole, triticonazole; cyazofamid, prochloraz, ethaboxam, fluazinam, cyprodinil, pyrimethanil; triforine; fludioxonil, dodemorph, fenpropimorph, tridemorph, vinclozolin, dazomet, fenoxanil, fenpropidin, proquinazid; flubenthiavalicarb, iprovalicarb, dodine, dithianon, fosetyl, fosetyl-aluminum, chlorothalonil, spiroxamine, cyflufenamid, cymoxanil, metrafenone.

More preferred fungicides are azoxystrobin, dimoxystrobin, fluoxastrobin, kresoximmethyl, picoxystrobin, pyraclostrobin, trifloxystrobin, orysastrobin, boscalid, metalaxyl, N-(3',4'-dichloro-4-fluorobiphenyl-2-yl)-3-difluoromethyl-1-methylpyrazole-4-carboxamide, dimethomorph, fluopicolide (picobenzamid), zoxamide; mandipropamid: N-(3',4'-dichloro-5-fluorobiphenyl-2-yl)-3-difluoromethyl-1-methylpyrazole-4-carboxamide, 3-Difluoromethyl-1-methyl-1H-pyrazole-4-carboxylic acid (2-bicyclopropyl-2- yl-phenyl)-amide, cyproconazole, difenoconazole, epoxiconazole, metconazole, propiconazole, prothioconazole, tebuconazole, cyazofamid, prochloraz, cyprodinil, triforine; fludioxonil, dodemorph, fenpropimorph, tridemorph, vinclozolin, dazomet, fenoxanil, iprovalicarb, dodine, dithianon, fosetyl, fosetyl-aluminum, chlorothalonil, spiroxamine, metrafenone.

Most preferred fungicides are azoxystrobin, fluoxastrobin, picoxystrobin, pyraclostrobin, trifloxystrobin, orysastrobin, boscalid, metalaxyl, N-(3',4'-dichloro-4-fluorobiphenyl-2-yl)-3-difluoromethyl-1-methylpyrazole-4-carboxamide, dimethomorph, fluopicolide (picobenzamid), zoxamide; mandipropamid, 3-Difluoromethyl-1-methyl-1H-pyrazole-4-carboxylic acid (2-bicyclopropyl-2-yl-phenyl)-amide, cyproconazole, difenoconazole, epoxiconazole, propiconazole, prothioconazole, tebuconazole, prochloraz, cyprodinil, fludioxonil, iprovalicarb, fosetyl, fosetyl-aluminum, chlorothalonil, spiroxamine, metrafenone.

As mentioned above, in one embodiment of the invention, also pesticides can be used, which confer plant health effects. Such pesticides are known in the art. Suitable for this purpose are, for example an active compound that inhibits the mitochondrial breathing chain at the level of the b/c1 complex;

carboxylic amides selected from benalaxyl, benodanil, boscalid, carboxin, mepronil, fenfuram, fenhexamid, flutolanil, furametpyr, metalaxyl, ofurace, oxadixyl, oxycarboxin, penthiopyrad, thifluzamid, tiadinil, 4-difluoromethyl-2-methyl-thiazol-5-carboxylic acid-(4'-bromo-biphenyl-2-yl)-amide, 4-difluoromethyl-2-methyl-thiazol-5-carboxylic acid-(4'-trifluoromethyl-biphenyl-2-yl)-amide, 4-difluoromethyl-2-methyl-thiazol-5-carboxylic acid-(4'-chloro-3'-fluoro-biphenyl-2-yl)-amide, 3-difluoromethyl-1-methyl-pyrazol-4-carboxylic acid-(3',4'-dichloro-4-fluoro-biphenyl-2-yl)-amide, 3,4-dichloro-isothiazol-5-carboxylic acid-(2-cyano-phenyl)-amide, dimethomorph, flumorph, flumetover, fluopicolide (picobenzamid), zoxamide, carpropamide, diclocymet, mandipropamid, N-(2-(4-[3-(4-chloro-phenyl)-prop-2-inyloxy]-3-methoxy-phenyl)-ethyl)-2-methanesulfonylamino-3-methyl-butyramid and N-(2-(4-[3-(4-chloro-phenyl)-prop-2-inyloxy]-3-methoxyphenyl)-ethyl)-2-ethanesulfonylamino-3-methyl-butyramide;

azoles selected from bitertanole, bromuconazole, cyproconazole, difenoconazole, diniconazole, enilconazole, epoxiconazole, fenbuconazole, flusilazole, fluquinconazole, flutriafol, hexaconazole, imibenconazole, ipconazole, metconazole, myclobutanil, penconazole, propiconazole, prothioconazole, simeconazole, tebuconazole, tetraconazole, triadimenol, triadimefon, triticonazole, cyazofamid, imazalil, pefurazoate, prochloraz, triflumizol, benomyl, carbendazim, fuberidazole, thiabendazole, ethaboxam, etridiazole and hymexazole;

nitrogen-containing heterocyclic compounds selected from fluazinam, pyrifenox, 3-[5-(4-chloro-phenyl)-2,3-dimethyl-isoxazolidin-3-yl]-pyridine, bupirimat, cyprodinil, ferimzon, fenarimol, mepanipyrim, nuarimol, pyrimethanil, triforin, fludioxonil, fenpiclonil, aldimorph, dodemorph, fenpropimorph, tridemorph, iprodion, procymidon, vinclozolin, acibenzolar-5-methyl, anilazin, captan, captafol, dazomet, diclomezine, fenoxanil, folpet, fenpropidin, famoxadone, fenamidone, octhilonon, probenazol, proquinazid, pyroquilon, quinoxyfen, tricyclazol, 2-butoxy-6-iodo-3-propyl-chromen-4-one, 3-(3-bromo-6-fluoro-2-methyl-indole-1-sulfonyl)-[1,2,4]triazole-1-sulfonic acid dimethylamide;

carbamates and dithiocarbamates selected from ferbam, mancozeb, metiram, metam, propineb, thiram, zineb, ziram, diethofencarb, flubenthiavalicarb, iprovalicarb, propamocarb, 3-(4-chloro-phenyl)-3-(2-isopropoxycarbonylamino-3-methyl-butyrylamino)-propionic acid methylester and N-(1-(1-(4-cyanophenyethanesulfonyl)-but-2-yl) carbamic acid-(4-fluorophenyl)ester;

guanidines selected from dodin, iminoctadine and guazatin;

antibiotics selected from kasugamycin, polyoxine, streptomycin and validamycin A;

fentin salts;

sulfur-containing heterocyclic compounds selected from isoprothiolan and dithianon; organophosphorous compounds selected from edifenphos, fosetyl, fosetyl-aluminium, iprobenfos, pyrazophos, tolclofos-methyl, phosphoric acid and the salts thereof;

organo-chloro compounds selected from thiophanate methyl, chlorothalonil, dichlofluanid, tolylfluanid, flusulfamid, phthalide, hexachlorbenzene, pencycuron, quintozen;

nitrophenyl derivatives selected from binapacryl, dinocap and dinobuton;

inorganic active ingredients selected from Bordeaux composition, copper acetate, copper hydroxide, copper oxychloride, basic copper sulfate and sulfur;

spiroxamine; cyflufenamide; cymoxanil; metrafenone; organo(thio)phosphates selected from acephate, azamethiphos, azinphos-methyl, chlorpyrifos, chlorpyrifos-methyl, chlorfenvinphos, diazinon, dichlorvos, dicrotophos, dimethoate, disulfoton, ethion, fenitrothion, fenthion, isoxathion, malathion, methamidophos, methidathion, methyl-parathion, mevinphos, monocrotophos, oxydemeton-methyl, paraoxon, parathion, phenthoate, phosalone, phosmet, phosphamidon, phorate, phoxim, pirimiphos-methyl, profenofos, prothiofos, sulprophos, tetrachlorvinphos, terbufos, triazophos and trichlorfon;

carbamates selected from alanycarb, aldicarb, bendiocarb, benfuracarb, carbaryl, carbofuran, carbosulfan, fenoxycarb, furathiocarb, methiocarb, methomyl, oxamyl, pirimicarb, propoxur, thiodicar and triazamate;

pyrethroids selected from allethrin, bifenthrin, cyfluthrin, cyhalothrin, cyphenothrin, cypermethrin, alpha-cypermethrin, beta-cypermethrin, zeta-cypermethrin, deltamethrin, esfenvalerate, etofenprox, fenpropathrin, fenvalerate, imiprothrin, lambda-cyhalothrin, permethrin, prallethrin, pyrethrin I and II, resmethrin, silafluofen, tau-fluvalinate, tefluthrin, tetramethrin, tralomethrin, transfluthrin and profluthrin, dimefluthrin;

growth regulators selected from a) chitin synthesis inhibitors that are selected from the benzoylureas chlorfluazuron, diflubenzuron, flucycloxuron, flufenoxuron, hexaflumuron, lufenuron, novaluron, teflubenzuron, triflumuron; buprofezin, diofenolan, hexythiazox, etoxazole and clofentazine; b) ecdysone antagonists that are selected from halofenozide, methoxyfenozide, tebufenozide and azadirachtin; c) juvenoids that are selected from pyriproxyfen, methoprene and fenoxycarb and d) lipid biosynthesis inhibitors that are selected from spirodiclofen, spiromesifen and spirotetramat; nicotinic receptor agonists/antagonists compounds selected from clothianidin, dinotefuran, (EZ)-1-(6-chloro-3-pyridylmethyl)-N-nitroimidazolidin-2-ylideneamine (imidacloprid), (EZ)-3-(2-chloro-1,3-thiazol-5-ylmethyl)-5-methyl-1,3,5-oxadiazinan-4-ylidene(nitro)amine (thiamethoxam), nitenpyram, acetamiprid, thiacloprid; the thiazol compound of formula (I¹)

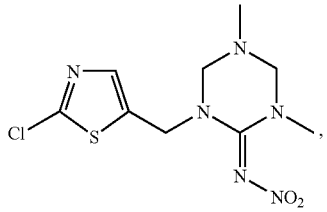

GABA antagonist compounds selected from acetoprole, endosulfan, ethiprole, 5-amino-1-(2,6-dichloro-α,α,α-trifluoro-p-tolyl)-4-trifluoromethylsulfinylpyrazole-3-carbonitrile (fipronil), vaniliprole, pyrafluprole, pyriprole and the phenylpyrazole compound of formula I²

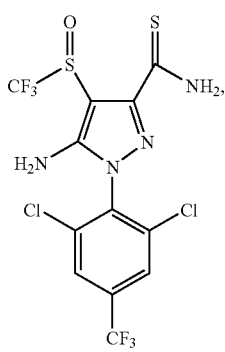

METI I compounds selected from fenazaquin, pyridaben, tebufenpyrad, tolfenpyrad and flufenerim;

METI II and III compounds selected from acequinocyl, fluacyprim and hydramethylnon;

chlorfenapyr;

oxidative phosphorylation inhibitor compounds selected from cyhexatin, diafenthiuron, fenbutatin oxide and propargite;

cyromazine; piperonyl butoxide; indoxacarb; benclothiaz, bifenazate, cartap, flonicamid, pyridalyl, pymetrozine, sulfur, thiocyclam, flubendiamide, cyenopyrafen, flupyrazofos, cyflumetofen, amidoflumet, the aminoquinazolinone compound of formula I⁴

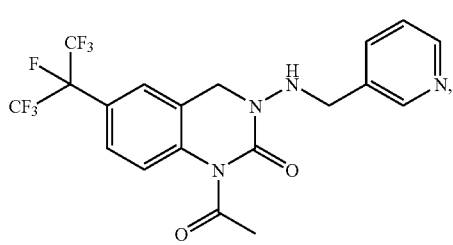

and anthranilamide compounds of formula I⁵

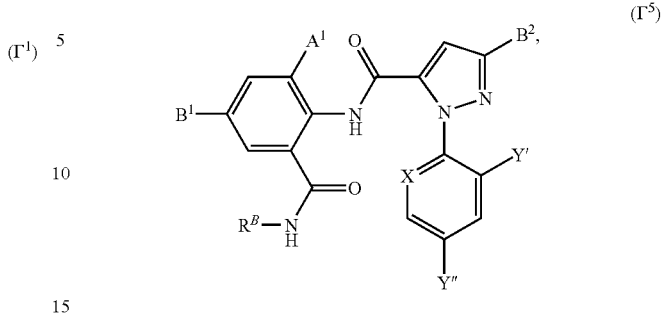

wherein $A^1$ is $CH_3$, Cl, Br, I, X is C—H, C—Cl, C—F or N, Y' is F, Cl, or Br, Y'' is F, Cl, $CF_3$, $B^1$ is hydrogen, Cl, Br, I, CN, $B^2$ is Cl, Br, $CF_3$, $OCH_2CF_3$, $OCF_2H$, and $R^B$ is hydrogen, $CH_3$ or $CH(CH_3)_2$.

wherein pyraclostrobin, azoxystrobin, kresoximmethyl, trifloxystrobin, picoxystrobin, dimoxystrobin, fluoxastrobin, orysastrobin, tebuconazole, difenoconazole, epoxiconazole, cyproconazole, prothioconazol, propiconazole, fipronil, imidacloprid and thiamethoxam are preferred.

As set forth above, the polymers according to the present invention can be used for the preparation of formulations comprising at least one pesticide and the polymer according to the present invention. Optionally, formulations comprising at least one pesticide and at least one polymer according to the present invention may comprise further formulation auxiliaries.

In general, the formulations comprise from 0 to 90% by weight, preferably from 1 to 85% by weight, more preferably from 5 to 80% by weight, most preferably from 5 to 65% by weight of the formulation auxiliaries.

The term "formulation auxiliaries" within the meaning of the invention is auxiliaries suitable for the formulation of pesticides, such as further solvents and/or carriers and/or surfactants (ionic or non-ionic surfactants, adjuvants, dispersing agents) and/or preservatives and/or antifoaming agents and/or anti-freezing agents and optionally, for seed treatment formulations colorants and/or binders and/or gelling agents and/or thickeners.

Examples of suitable solvents are water, aromatic solvents (for example Solvesso products, xylene), paraffins (for example mineral oil fractions such as kerosene or diesel oil), coal tar oils and oils of vegetable or animal origin, aliphatic, cyclic and aromatic hydrocarbons, for example toluene, xylene, paraffin, tetrahydronaphthalene, alkylated naphthalenes or their derivatives, alcohols (for example methanol, butanol, pentanol, benzyl alcohol, cyclohexanol), ketones (for example cyclohexanone, gamma-butyrolactone), pyrrolidones (NMP, NEP, NOP), acetates (glycol diacetate), glycols, fatty acid dimethylamides, fatty acids and fatty acid esters, isophorone and dimethylsulfoxide. In principle, solvent mixtures may also be used.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol and formaldehyde, polyoxyethylene octylphenol ethers, ethoxylated isooctylphenol, octylphenol, nonylphenol, alkylphenol polyglycol ethers, tributylphenyl polyglycol ethers, tristearylphenyl polyglycol ethers, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors and methylcellulose.

Examples of suitable carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders, polyvinylpyrrolidone and other solid carriers.).

Also anti-freezing agents such as glycerin, ethylene glycol, hexylene glycol, propylene glycol and bactericides such as can be added to the formulation.

Suitable antifoaming agents are for example antifoaming agents based on silicon or magnesium stearate.

Suitable preservatives are for example 1,2-benzisothiazolin-3-one and/or 2-Methyl-2H-isothiazol-3-one or sodium benzoate or benzoic acid.

Examples of thickeners (i.e., compounds which bestow a pseudoplastic flow behavior on the formulation, i.e. high viscosity at rest and low viscosity in the agitated state) are, for example, polysaccharides or organic or inorganic layered minerals, such as xanthan gum (Kelzan® from Kelco), Rhodopol® 23 (Rhone-Poulenc) or Veegum® (R. T. Vanderbilt) or Attaclay® (Engelhardt).

Seed Treatment formulations may additionally comprise binders and optionally colorants.

Optionally, also colorants can be included in the formulation. Suitable colorants or dyes for seed treatment formulations are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Binders can be added to improve the adhesion of the active materials on the seeds after treatment. Suitable binders are: polyvinylpyrrolidone, polyvinylacetate, polyvinylalkohol and tylose.

The use forms of the formulations (for example in the form of directly sprayable solutions, powders, suspensions or dispersions, emulsions, oil dispersions, pastes, dustable products, materials for spreading, or granules) depend entirely on the intended purposes; they are intended to ensure in each case the finest possible distribution of the pesticide and polymer according to the invention.

Examples of suitable formulation types in which the polymer according to the present invention can be used are
1. Liquid Formulations such as
EC (Emulsifiable concentrate) formulation; SL or LS (Soluble concentrate) formulation; EW (Emulsion, oil in water) formulation ME (Microemulsion) formulation MEC Microemulsifiable concentrates concentrate formulation CS (Capsule suspension) formulation TK (Technical concentrate) formulation, OD (oil based suspension concentrate) formulation; SC (suspension concentrate) formulation; SE (Suspo-emulsion) formulation; ULV (Ultra-low volume liquid) formulation; SO (Spreading oil) formulation; AL (Any other liquid) formulation; LA (Lacquer) formulation; DC (Dispersible concentrate) formulation;
2. Solid Formulations such as
WG (Water dispersible granules) formulation; TB (Tablet) formulation; FG (Fine granule) formulation; MG (Microgranule) formulation; SG (soluble Granule)

Preferred are formulation types such as EC (Emulsifiable concentrate) formulation; SL or LS (Soluble concentrate) formulation; EW (Emulsion, oil in water) formulation ME (Microemulsion) formulation, CS (Capsule suspension) formulation, OD (oil based suspension concentrate) formulation; SC (suspension concentrate) formulation; SE (Suspo-emulsion) formulation; DC (Dispersible concentrate) formulation, WG (Water dispersible granules) formulation; TB (Tablet) formulation); FG (Fine granule) formulation and SG (soluble Granule).

Especially preferred are all formulations that are suitable for seed treatment or soil treatment (for example for in furrow treatment), wherein formulations for seed treatment are most preferred.

The invention also includes a process for the preparation of a formulation according to the present invention. The processes used in this connection are generally familiar to a person skilled in the art and are, for example, described in the literature cited with the various formulation types (see e.g. for review U.S. Pat. No. 3,060,084, EP-A 707 445 (for liquid concentrates), Browning, "Agglomeration", Chemical Engineering, Dec. 4, 1967, 147-48, Perry's Chemical Engineer's Handbook, 4th Ed., McGraw-Hill, New York, 1963, pages 8-57 and et seq. WO 91/13546, U.S. Pat. No. 4,172,714, U.S. Pat. No. 4,144,050, U.S. Pat. No. 3,920,442, U.S. Pat. No. 5,180,587, U.S. Pat. No. 5,232,701, U.S. Pat. No. 5,208,030, GB 2,095,558, U.S. Pat. No. 3,299,566, Klingman, Weed Control as a Science, John Wiley and Sons, Inc., New York, 1961, Hance et al., Weed Control Handbook, 8th Ed., Blackwell Scientific Publications, Oxford, 1989 and Mollet, H., Grubemann, A., Formulation technology, Wiley VCH Verlag GmbH, Weinheim (Germany), 2001, 2. D. A. Knowles, Chemistry and Technology of Agrochemical Formulations, Kluwer Academic Publishers, Dordrecht, 1998 (ISBN 0-7514-0443-8).

Liquid formulations can be prepared by mixing or combining the polymer according to the invention with at least one pesticide and or further formulation auxiliaries.

Powders, materials for spreading and dustable products can be prepared by mixing or concomitantly grinding the active substances with a solid carrier.

Granules, for example coated granules, impregnated granules and homogeneous granules, can be prepared by binding the active compounds to solid carriers.

The above-referred formulations can be used as such or use forms prepared therefrom, for example in the form of directly sprayable solutions, powders, suspensions or dispersions, emulsions, oil dispersions, pastes, dustable products, materials for spreading, or granules, by means of spraying, atomizing, dusting, spreading or pouring. The use forms depend entirely on the intended purposes; it is intended to ensure in each case the finest possible distribution of the pesticid(es) and polymer according to the invention.

Aqueous use forms can be prepared also from emulsion concentrates, pastes or wettable powders (sprayable powders, oil dispersions) by adding a suitable solvent, for example water.

The addition of the polymer to the formulation can be performed prior or after dilution of the formulation in water;

e.g. preparing a formulation as mentioned before containing the polymer according to this invention or adding the polymer after dilution of the pesticide formulation in a suitable solvent, for example water (e.g. as so called tank mix).

All embodiments of the above-mentioned application are herein below referred to as "formulation according to the present invention".

The present invention furthermore comprises a method of combating harmful insects and/or phytopathogenic fungi, which comprises contacting seed or soil or habitat of plants in or on which the harmful insects and/or phytopathogenic fungi are growing or may grow, seed or soil to be protected from attack or infestation by said harmful insects and/or phytopathogenic fungi with an effective amount of a agrochemical formulation according to the present invention.

The formulations according to the present invention can therefore be used for the control of a multitude of phytopaghogenic fungi or insects on various cultivated plants or weeds in, such as wheat, rye, barley, oats, rice, corn, grass, bananas, cotton, soya, coffee, sugar cane, vines, fruits and ornamental plants, and vegetables, such as cucumbers, beans, tomatoes, potatoes and cucurbits, and on the seeds of these plants.

The present invention also comprises a method of controlling undesired vegetation, which comprises contacting soil or habitat of plants with a herbicidally effective amount of a formulation according to the present invention.

The present invention furthermore comprises a method of improving the health of plants, which comprises applying a formulation according to the present invention, wherein the pesticide is a pesticide which confers plant health effects, to plants, parts of plants, or the locus where plants grow.

The present invention furthermore comprises a method of controlling undesired vegetation, which comprises allowing a herbicidally effective amount of a agrochemical formulation according to the present invention to act on habitat or on seed of plants.

Thus, the formulations according to the present invention compositions according to the present invention are suitable for controlling common harmful plants in useful plants, in particular in crops such as oat, barley, millet, corn, rice, wheat, sugar cane, cotton, oilseed rape, flax, lentil, sugar beet, tobacco, sunflowers and soybeans or in perennial crops.

The term phytopathogenic fungi includes but is not limited to the following species:
*Alternaria* species on vegetables, rapeseed, sugar beet and fruit and rice (for example *A. solani* or *A. alternate* on potato and other plants); *Aphanomyces* species on sugar beet and vegetables; *Bipolaris* and *Drechslera* species on corn, cereals, rice and lawns (for example *D. teres* on barley, *D. tritci-repentis* on wheat); *Blumeria graminis* (powdery mildew) on cereals; *Botrytis cinerea* (gray mold) on strawberries, vegetables, flowers and grapevines; *Bremia lactucae* on lettuce; *Cercospora* species on corn, soybeans, rice and sugar beet (for example *C. beticula* on sugar beet); *Cochliobolus* species on corn, cereals, rice (for example *Cochliobolus sativus* on cereals, *Cochliobolus* miyabeanus on rice); *Colletotricum* species on soybeans, cotton and other plants (for example *C. acutatum* on various plants); Esca on grapes caused by *Phaeoacremonium chlamydosporium, Ph. Aleophilum*, and *Formitipora punctata* (syn. *Phellinus punctatus*); *Exserohilum* species on corn; *Erysiphe cichoracearum* and *Sphaerotheca fuliginea* on cucurbits; *Fusarium* and *Verticillium* species (for example *V. dahliae*) on various plants (for example *F. graminearum* on wheat); *Gaeumanomyces graminis* on cereals; *Gibberella* species on cereals and rice (for example *Gibberella fujikuroi* on rice); Grainstaining complex on rice; *Helminthosporium* species (for example *H. graminicola*) on corn and rice; *Michrodochium nivale* on cereals; *Mycosphaerella* species on cereals, bananas and peanuts (*M. graminicola* on wheat, *M. fijiesis* on bananas); *Phakopsara pachyrhizi* and *Phakopsara meibomiae* on soybeans; *Phomopsis* species on soybeans, sunflowers and grapevines (*P. viticola* on grapevines, *P. helianthii* on sunflowers); *Phytophthora infestans* on potatoes and tomatoes; *Plasmopara viticola* on grapevines; *Podosphaera leucotricha* on apples; *Pseudocercosporella herpotrichoides* on cereals; *Pseudoperonospora* species on hops and cucurbits (for example *P. cubenis* on cucumbers); *Puccinia* species on cereals, corn and asparagus (*P. triticina* and *P. striformis* on wheat, *P. asparagi* on asparagus); *Pyrenophora* species on cereals; *Pyricularia oryzae, Corticium sasakii, Sarocladium oryzae, S. attenuatum, Entyloma oryzae* on rice; *Pyricularia grisea* on lawns and cereals; *Pythium* spp. on lawns, rice, corn, cotton, rapeseed, sunflowers, sugar beet, vegetables and other plants; *Rhizoctonia*-species (for example *R. solani*) on cotton, rice, potatoes, lawns, corn, rapeseed, potatoes, sugar beet, vegetables and other plants; *Rhynchosporium secalis* e.g. on rye and barley; *Sclerotinia* species (for example *S. sclerotiorum*) on rapeseed, sunflowers and other plants; *Septoria tritici* and *Stagonospora nodorum* on wheat; *Erysiphe* (syn. *Uncinula necator*) on grapevines; *Setospaeria* species on corn and lawns; *Sphacelotheca reilinia* on corn; *Thievaliopsis* species on soybeans and cotton; *Tilletia* species on cereals; *Ustilago* species on cereals, corn and sugar beet and; *Venturia* species (scab) on apples and pears (for example *V. inaequalis* on apples). They are particularly suitable for controlling harmful fungi from the class of the *Oomycetes*, such as *Peronospora* species, *Phytophthora* species, *Plasmopara viticola* and *Pseudoperonospora* species.

The formulations according to the present invention can also be used for controlling harmful fungi in the protection of material such as wood. Examples of fungi are Ascomycetes, such as *Ophiostoma* spp., *Ceratocystis* spp., *Aureobasidium pullulans, Sclerophoma* spp., *Chaetomium* spp., *Humicola* spp., *Petriella* spp., *Trichurus* spp.; Basidiomycetes, such as *Coniophora* spp., *Coriolus* spp., *Gloeophyllum* spp., *Lentinus* spp., *Pleurotus* spp., *Poria* spp., *Serpula* spp. and *Tyromyces* spp., Deuteromycetes, such as *Aspergillus* spp., *Cladosporium* spp., *Penicillium* spp., *Trichoderma* spp., *Alternaria* spp., *Paecilomyces* spp. and Zygomycetes, such as *Mucor* spp., The invention furthermore relates to a method for controlling undesirable vegetation in crops, in particular in crops of oat, barley, millet, corn, rice, wheat, sugar cane, cotton, oilseed rape, flax, lentil, sugar beet, tobacco, sunflowers and soybeans or in perennial crops, which comprises allowing a effective amount of a agrochemical formulation according to the present invention to act on plants, their habitat or on seed of said plants.

The invention furthermore relates to a method for controlling undesirable vegetation in crops which, by genetic engineering or by breeding, are resistant to one or more herbicides and/or fungicides and/or or to attack by insects, which comprises allowing a effective amount of a agrochemical formulation according to the present invention to act on plants, their habitat or on seed of said plants.

The control of undesired vegetation is understood as meaning the destruction of weeds. Weeds, in the broadest sense, are understood as meaning all those plants which grow in locations where they are undesired, for example:

Dicotyledonous weeds of the genera: *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus, Taraxacum.*

Monocotyledonous weeds of the genera: *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristyslis, Sagittaria, Eleocharis, Scirpus, Paspalum, Ischaemum, Sphenoclea, Dactyloctenium, Agrostis, Alopecurus, Apera.*

Thus, as set forth above, formulations according to the invention can be applied via various methods.

One embodiment of the present invention comprises soil treatment, e.g by spraying or dusting or otherwise applying the mixture to the soils before (e.g. by soil drench) or after sowing of the plants or before or after emergence of the plants.

In accordance with one specific variant of soil application, a further subject of the invention is a method of treating soil by the application, in particular into the seed drill.

In accordance with one other specific variant of soil application, a further subject of the invention is in furrow treatment, which comprises adding a solid or liquid formulation to the open furrow, in which seeds have been sown or, alternatively, applying seeds and formulation simultaneously to the open furrow.

A preferred embodiment of the present invention comprises the treatment of seeds or seedlings from plants.

The term seed treatment comprises all suitable seed treatment techniques known in the art, such as seed dressing, seed coating, seed dusting, seed soaking and seed pelleting.

Thus, the application of the formulation according to the present invention is carried out by spraying or dusting or otherwise applying the formulation according to the present invention to the seeds or the seedlings.

The present invention also comprises seeds coated with formulation according to the present invention.

The term seed embraces seeds and plant propagules of all kinds including but not limited to true seeds, seed pieces, suckers, corms, bulbs, fruit, tubers, grains, cuttings, cut shoots and the like and means in a preferred embodiment true seeds.

Suitable seed is seed of cereals, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

In addition, the formulation according to the invention may also be used for the treatment seeds from plants, which tolerate the action of herbicides or fungicides or insecticides owing to breeding, including genetic engineering methods, for example seeds of transgenic crops which are resistant to herbicides from the group consisting of the sulfonylureas (EP-A-0257993, U.S. Pat. No. 5,013,659), imidazolinones (see for example U.S. Pat. No. 6,222,100, WO0182685, WO0026390, WO9741218, WO9802526, WO9802527, WO 04/106529, WO 05/20673, WO 03/14357, WO 03/13225, WO 03/14356, WO 04/16073), glufosinate-type (see for example EP-A-0242236, EP-A-242246) or glyphosate-type (see for example WO 92/00377) or in seeds of plants resistant towards herbicides selected from the group of cyclohexadienone/Aryloxyphenoxypropionic acid herbicides (U.S. Pat. No. 5,162,602, U.S. Pat. No. 5,290,696, U.S. Pat. No. 5,498,544, U.S. Pat. No. 5,428,001, U.S. Pat. No. 6,069,298, U.S. Pat. No. 6,268,550, U.S. Pat. No. 6,146,867, U.S. Pat. No. 6,222,099, U.S. Pat. No. 6,414,222) or in seeds of transgenic crop plants, for example cotton, with the capability of producing *Bacillus thuringiensis* toxins (Bt toxins) which make the plants resistant to certain pests (EP-A-0142924, EP-A-0193259)

The seed treatment application of the formulation according to the invention is carried out by spraying or dusting the seeds before sowing of the plants and before emergence of the plants by methods known to the skilled artisan.

In the treatment of seeds the corresponding formulations are applied by treating the seeds with an effective amount of the formulation according to the present invention. Herein, the application rates of pesticide are generally from 0.1 g to 10 kg per 100 kg of seed, preferably from 1 g to 5 kg per 100 kg of seed, in particular from 1 g to 2.5 kg per 100 kg of seed. For specific crops such as lettuce or onion, the rate can be higher.

The invention is further illustrated but not limited by the following examples.

EXAMPLES

To prepare the polymers, the following apparatus was used:

1 l apparatus with process controlled water-bath, anchor stirrer and thermometer. The apparatus had connectors for 3 feeds, a reflux condenser and an inlet tube for introducing nitrogen or steam.

ABBREVIATIONS USED

MA maleic anhydride
S styrene
MeHQ hydrochinon monomethylether
VP vinyl pyrrolidone
$C_{20-24}$ olefin linear 1-alkene, technical mixture of $C_{20}$, $C_{22}$, $C_{24}$ alkenes, 1-alkene content >85 wt %
Lutensol TO 3 nonionic surfactant, ethoxylated saturated iso-$C_{13}$ alcohol of the formula iso-$C_{13}H_{27}O(CH_2CH_2O)_3$ The polymers can be synthesized by two different reaction ways (procedure 1 and procedure 2):

Example 1

Procedure 1

In a first step the MA copolymer is synthesised or a suitable copolymer is purchased. This polymer is then esterified in a second step.

Preparation of Polymer A

Synthesis of a MA/S copolymer (molar ratio 50/50) esterified with a $C_{13}$-fatty alcohol alkoxylate (50% of the MA units are esterified).

The reaction vessel (100 g MA/S copolymer*, 575 g $C_{13}$-fatty alcohol alkoxylate) was gassed with nitrogen and heated to 150° C. internal temperature. The reaction mixture was then stirred for 4 hours at this temperature.

Example 2

Preparation of Polymers B-F

The preparation of polymers B-F was carried out analogously to example 1. The amounts and substances used for reaction vessel are set forth in table 1.

TABLE 1

| | vessel |
|---|---|
| Polymer B | 47.56 g MA/S copolymer*<br>120 g nonylphenol ethoxylate |
| Polymer C | 94.4 g MA/S copolymer*<br>467 g iso-C13-alcool ethoxylat |
| Polymer D | 47.56 g MA/S copolymer*<br>90 g nonylphenol ethoxylate |
| Polymer E | 105.77 g MA/$C_{20-24}$-olefin copolymer<br>134.22 g Pluriol A 1000 E |
| Polymer F | 164 g MA/VP copolymer<br>200 g Lutensol TO 3 |

*The MA/S (50:50 mol %) copolymer with the tradename SMA 100 F was purchased from Sartomer.

Example 3

Procedure 2

The MA copolymer is synthesized in presence of the esterification agent. In this case esterification takes place during polymerisation.

Preparation of Polymer A

The initial charge (345 g $C_{13}$-fatty alcohol alkoxylate, 98.06 g MA) was gassed with nitrogen and heated to 95° C. internal temperature. After stirring the initial charge for 10 minutes at this temperature feed 1 (104.15 g S, 0,544 g MeHQ) and 2 (6.22 g tert. butyl peroctoate, 230 g $C_{13}$-fatty alcohol alkoxylat) are started. Feed 1 was introduced during 2 hours, feed 2 was introduced during 2 hours 15 minutes. After introduction of feed 2 was complete the reaction mixture was stirred for 1 hour at 95° C., after this it was heated up to 120° C. and was stirred for additional 4 hours.

Example 4

Preparation of Polymer B-D

The preparation of polymers B-D was carried out analogously to example 3. The amounts and substances used for initial charge, feed 1 and 2 are set forth in table 2.

TABLE 2

| | Initial charge | Feed 1 | Feed 2 |
|---|---|---|---|
| Polymer B | 525 g nonylphenol ethoxylate<br>49.03 g MA | 52.1 g S<br>0.27 g MeHQ | 3.1 g tert. butyl peroctoate |
| Polymer C | 500 g iso-C13-alcool ethoxylat<br>49.03 g MA | 52.1 g S<br>0.53 g MeHQ | 3.1 g tert. butyl peroctoate |
| Polymer D | 394 g nonylphenol ethoxylate<br>49.03 g MA | 52.1 g S<br>0.27 g MeHQ | 3.1 g tert. butyl peroctoate |

Example 5 A

Root Uptake

To test the root systemicity of metaflumizone with polymers, radioactively marked metaflumizone (prepared in analogy to methods known in the art, based on $^{14}C$ marked benzene) was used. For the tests wheat plants were grown in vermiculite and then transferred to a container with 1.5 ml of a metaflumizone/polymer (1:1 wt) solution in a water/acetone mixture [30 μl cold active solution (10000 ppm stock solution in acetone), 24 μl hot active solution (0.1 ppm in acetone, 1 μl corresponds to ~26000 Bcq), 30 μl acetone and 30 μl polymer solution (10000 ppm stock solution in water) were mixed and refilled with water to 10 ml)]. As reference metaflumizone solutions in water/acetone without polymer were used. After 48 and 120 hours leafs were cut from the plant and dissolved in Soluene 350 (60-80% tolouene, 20-40% dodecyl(dimethyl)-(tetradecyl)ammonium hydroxide, 2.5-10% methanol). Afterwards the radioactivity in the plant material was measured. High radioactivity in the plant material corresponds to high active ingredient uptake.

The results are presented in table 3

TABLE 3

| | Time to measurement [h] | Uptake [Bcq] |
|---|---|---|
| Reference | 120 | 120 |
| Polymer A | 120 | 163 |

The results show that with polymer A significantly improved root uptake was achieved after 120 hours.

Example 5 B

Root Uptake

To test the root systemicity of fipronil with polymers, wheat plants in vermiculite were drenched with 20 ml fipronil/polymer (1:1 wt) solutions in hoagland solution/acetone mixtures (0.6 v % acetone). Two fipronil and polymer concentrations were used, 3 ppm and 6 ppm. As reference fipronil solutions in Hoagland solution/acetone mixtures without polymer were used.

Hoagland solution consists of the following ingredients: 0.25 v % of 1M $KNO_3$ solution in water, 0.1 v % of 1M $MgSO_4$ solution in water, 0.05 v % of 1M $KH_2PO_4$ solution in water, 0.25 v % 1M $Ca(NO_3)_2$) solution in water 0.05 v % of a trace solution consisting of 2.86 g/l $H_3BO_3$, 1.81 g/l $MnCl_2$*$4H_2O$, 0.22 g/l $ZnSO_4$*$7H_2O$, 0.08 g/l $CuSO_4$*$5H_2O$, 0.016 g/l $MoO_3$ in water, 0.05 v % Sequestrone 138 Fe consisting of 30 g/l sodium ferric ethylenediamine di-(o-hydroxyphenylacetate) in water, 99.225% water sterilized and pH-adjusted to 6-6.5 with NaOH.

The plants were then infested with aphids. After 4 days the aphid population on the wheat plants was counted. The results of fipronil and fipronil with polymer are related to the aphid population on plants that had not been treated with fipronil. Results are presented in table 4.

TABLE 4

| | Concentration [ppm] | Aphid population |
|---|---|---|
| Not treated | 0 | 100% |
| reference | 3 | 22% |
| | 6 | 12% |

TABLE 4-continued

|  | Concentration [ppm] | Aphid population |
|---|---|---|
| Polymer B | 3 | 2% |
|  | 6 | 4% |
| Polymer C | 3 | 1% |
|  | 6 | 0% |
| Polymer D | 3 | 12% |
|  | 6 | 9% |

The results show that with the polymers B to D, significant improved pest control twas achieved for both concentrations.

Example 5 C

Root Uptake

With polymer B additional tests in soil were performed. The soil was drenched with 29 ml of fipronil/polymer (1:1 wt) solutions in hoagland solution/acetone mixtures (0.6 v % acetone). Concentrations of 400 ppm, 200 ppm 100 ppm, 50 ppm, 25 ppm, 125 ppm, 6.25 ppm and 3.1 ppm were applied. As reference fipronil solutions in Hoagland solution/acetone mixtures without polymer were used.
Hoagland solution consists of the following ingredients
0.25 v % of 1M $KNO_3$ solution in water, 0.1 v % of 1M $MgSO_4$ solution in water, 0.05 v % of 1M $KH_2PO_4$ solution in water, 0.25 v % 1M $Ca(NO_3)_2$) solution in water, 0.05 v % of a trace solution consisting of 2.86 g/l $H_3BO_3$, 1.81 g/l $MnCl_2*4H_2O$, 0.22 g/l $ZnSO_4*7H_2O$, 0.08 g/l $CuSO_4*5H_2O$, 0.016 g/l $MoO_3$ in water, 0.075 v % Sequestrene 138 Fe consisting of 30 g/l sodium ferric ethylenediamine di-(o-hydroxyphenylacetate) in water, 99.225 v % water sterilized and pH adjusted to 6-6.5 with NaOH.

The plants were then infested with aphids. After 4 days the aphid populations on the wheat plants was counted. The results of fipronil and fipronil with polymer are related to the aphid population on plants that had not been treated with fipronil. Results are represented in table 5.

TABLE 5

|  | Concentration [ppm] | Aphid population |
|---|---|---|
| Not treated | 0 | 100% |
| reference | 400 | 0% |
|  | 200 | 0% |
|  | 100 | 5% |
|  | 50 | 14% |
|  | 25 | 18% |
|  | 12.5 | 21% |
|  | 6.25 | 31% |
|  | 3.1 | 50% |
| Polymer B | 400 | 0% |
|  | 200 | 0% |
|  | 100 | 5% |
|  | 50 | 0% |
|  | 25 | 10% |
|  | 12.5 | 9% |
|  | 6.25 | 12% |
|  | 3.1 | 10% |

The results show that with polymer B significantly improved pest control can be achieved in soil.

Example 6

Seed Treatment Tests

To test the polymers, 100 µL COSMOS® 50 FS (aqueous formulation for seed treatment containing 500 g/L Fipronil, commercially available from BASF) was mixed with 1100 µL of a 4.5 wt % polymer solution in water. As a reference ("COSMOS 50FS without polymer") a mixture of 100 µL COSMOS 50 FS in 1100 µL water was used. Then 100 sugar beet scads were treated twice with 300 µl polymer/COSMOS 50 FS mixture (corresponding to 25 g Fipronil/100 kg seed and 25 g polymer/100 kg seed), and another 100 seeds were treated twice with 300 µl of the reference ("COSMOS 50 FS without polymer").

The seeds of sugar-beets were sown in soil containing styropor-boxes under greenhouse conditions. Samples were taken at a plant height of about 10-15 cm. After sampling the plants (both treatment groups) were subdivided into two segments (hypocotyl and rest of plant). The samples frozen immediately after sampling and kept frozen until analysis. Prior to analyses the sample material was homogenized using a Stephansmill in the presence of dry ice resulting in very small sample particles.

Fipronil was extracted from plant matrices using a mixture of methanol and water. For clean-up a liquid/liquid partition against dichloromethane was used. The final determination of fipronil content was performed by HPLC-MS/MS. Results are presented in table 6.

TABLE 6

|  |  | Fipronil concentration [ppm] |
|---|---|---|
| COSMOS 50 FS without polymer | Hypocotyl | 0.1836 |
|  | Rest of plant | 0.0624 |
| COSMOS 50 FS with polymer A | Hypocotyl | 1.0195 |
|  | Rest of plant | 0.1185 |
| COSMOS 50 FS with polymer B | Hypocotyl | 1.5913 |
|  | Rest of plant | 0.1161 |

The results show that with the polymers A and B significantly improved root uptake was achieved in seed treatment experiments versus reference.

The invention claimed is:

1. A method of preparing a pesticide with increased systemicity comprising:
combining a pesticide with at least one co-polymer consisting of:
(a) at least one comonomer (a) selected from the group consisting of olefins, vinlyether, vinyl pyrrolidone and styrene; and
(b) at least one comonomer (b) selected from the group consisting of ethylenically unsaturated dicarboxylic mono and diesters, wherein said mono- or diester comprises an alcohol moiety having the structure of formula I

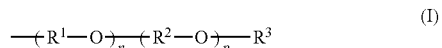

wherein
$R^1$ is 1,2-propylene or 2,3 propylene
$R^2$ is ethylene;
$R^3$ is branched or linear $C_1$-$C_{40}$, phenyl, phenyl substituted with $C_1$-$C_{20}$ alkyl, benzyl, or benzyl substituted with $C_1$-$C_{20}$ alkyl;
n corresponds to a value from 0 to 140;
p corresponds to a value from 0 to 100, wherein the sum of n and p is at least 1,
wherein the systemicity of the pesticide is increased.

2. The method of claim 1, wherein in the alcohol moiety of comonomer b) of formula I n is 0-50 and p is 1-60.

3. The method of claim 1, wherein in the alcohol moiety of comonomer b) of formula I $R^3$ is a phenyl radical which may be substituted or unsubstituted with 1, 2, 3 or 4 identical or different substituents L, wherein L is $C_1$-$C_{20}$ alkyl.

4. The method of claim 1, wherein in the alcohol moiety of comonomer b) of formula I $R^3$ is a nonylphenyl radical.

5. The method of claim 1, wherein comonomer (b) is a mono- or diester derived from unsaturated dicarboxylic acid with 4 to 8 carbon atoms.

6. The method of claim 1, wherein comonomer (b) is a mono- or diester of maleic acid.

7. The method of claim 1, wherein said pesticide provides plant health effects.

8. A method for treatment of seeds, which comprises applying to said seed a formulation comprising a pesticide and at least one co-polymer consisting of:
   (a) at least one comonomer (a) selected from the group consisting of olefins, vinlyether, vinyl pyrrolidone and styrene; and
   (b) at least one comonomer (b) selected from the group consisting of ethylenically unsaturated dicarboxylic mono and diesters, wherein said mono- or diester comprises an alcohol moiety having the structure of formula I

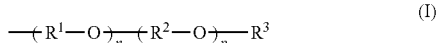

(I)

wherein
$R^1$ is 1,2-propylene or 2,3 propylene
$R^2$ is ethylene;
$R^3$ is hydrogen, branched or linear $C_1$-$C_{40}$, phenyl, phenyl substituted with $C_1$-$C_{20}$ alkyl, benzyl, or benzyl substituted with $C_1$-$C_{20}$ alkyl;
n corresponds to a value from 0 to 140;
p corresponds to a value from 0 to 100, wherein the sum of n and p is at least 1.

9. A method of combating harmful insects and/or phytopathogenic fungi, which comprises contacting seeds with an effective amount of an agrochemical formulation comprising a pesticide and at least one co-polymer consisting of:
   (a) at least one comonomer (a) selected from the group consisting of olefins, vinlyether, vinyl pyrrolidone and styrene; and
   (b) at least one comonomer (b) selected from the group consisting of ethylenically unsaturated dicarboxylic mono and diesters, wherein said mono- or diester comprises an alcohol moiety having the structure of formula I

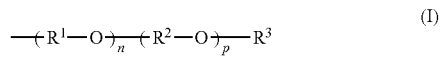

(I)

wherein
$R^1$ is 1,2-propylene or 2,3 propylene
$R^2$ is ethylene;
$R^3$ is hydrogen, branched or linear $C_1$-$C_{40}$, phenyl, phenyl substituted with $C_1$-$C_{20}$ alkyl, benzyl, or benzyl substituted with $C_1$-$C_{20}$ alkyl;
n corresponds to a value from 0 to 140;
p corresponds to a value from 0 to 100, wherein the sum of n and p is at least 1.

10. Seeds treated with a formulation comprising a pesticide and at least one co-polymer consisting of:
   (a) at least one comonomer (a) selected from the group consisting of olefins, vinlyether, vinyl pyrrolidone and styrene; and
   (b) at least one comonomer (b) selected from the group consisting of ethylenically unsaturated dicarboxylic mono and diesters, wherein said mono- or diester comprises an alcohol moiety having the structure of formula I

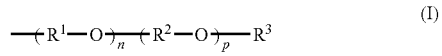

(I)

wherein
$R^1$ is 1,2-propylene or 2,3 propylene
$R^2$ is ethylene;
$R^3$ is hydrogen, branched or linear $C_1$-$C_{40}$, phenyl, phenyl substituted with $C_1$-$C_{20}$ alkyl, benzyl, or benzyl substituted with $C_1$-$C_{20}$ alkyl;
n corresponds to a value from 0 to 140;
p corresponds to a value from 0 to 100, wherein the sum of n and p is at least 1.

* * * * *